(12) United States Patent
Davis et al.

(10) Patent No.: US 11,830,581 B2
(45) Date of Patent: Nov. 28, 2023

(54) METHODS OF OPTIMIZING GENOME ASSEMBLY PARAMETERS

(71) Applicant: International Business Machines Corporation, Armonk, NY (US)

(72) Inventors: Matthew A. Davis, San Jose, CA (US); Mark Kunitomi, San Francisco, CA (US); Kun Hu, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 1301 days.

(21) Appl. No.: 16/295,836

(22) Filed: Mar. 7, 2019

(65) Prior Publication Data

US 2020/0286589 A1 Sep. 10, 2020

(51) Int. Cl.
*G16B 30/20* (2019.01)
*G16B 30/10* (2019.01)

(52) U.S. Cl.
CPC .............. *G16B 30/20* (2019.02); *G16B 30/10* (2019.02)

(58) Field of Classification Search
CPC ......... G16B 30/20; G16B 30/10; G16B 40/10
See application file for complete search history.

(56) References Cited

U.S. PATENT DOCUMENTS

| | | | |
|---|---|---|---|
| 8,209,130 | B1 | 6/2012 | Kennedy et al. |
| 8,352,195 | B2 | 1/2013 | Palmer et al. |
| 2011/0202280 | A1 | 8/2011 | Sikora et al. |
| 2014/0121985 | A1 | 5/2014 | Sayood et al. |
| 2014/0129152 | A1 | 5/2014 | Beer et al. |
| 2014/0188397 | A1 | 7/2014 | Fan et al. |
| 2015/0379196 | A1 | 12/2015 | Schnall-Levin et al. |

FOREIGN PATENT DOCUMENTS

| | | | |
|---|---|---|---|
| WO | 2010104608 A2 | 9/2010 | |
| WO | 2014028771 A1 | 2/2014 | |
| WO | WO-2014028771 A1 * | 2/2014 | ............. G06F 19/22 |

(Continued)

OTHER PUBLICATIONS

Zerbino, Daniel R., and Ewan Birney. "Velvet: algorithms for de novo short read assembly using de Bruijn graphs." Genome research 18.5 (2008): 821-829. (Year: 2008).*

(Continued)

*Primary Examiner* — Jesse P Frumkin
(74) *Attorney, Agent, or Firm* — Samuel Waldbaum; Cantor Colburn LLP

(57) ABSTRACT

An iterative process for optimizing one or more parameters used by a k-mer based de novo genome assembler program to assemble a set of sequenced nucleic acids is described. The method utilizes quality metrics whose desired values are initially specified. Computed values of the quality metrics are calculated during the assembly process and compared to the desired values. The assembly process stops when the computed values are not desired values. After modification of one or more of the parameters (e.g., k-mer value), the assembly process re-initiates using the modified parameter set. This process repeats until the computed values of the quality metrics meet the desired values. The final parameter set is then used to generate or complete one or more final assembled genomes.

21 Claims, 3 Drawing Sheets

(56) References Cited

FOREIGN PATENT DOCUMENTS

WO      2017139671 A1     8/2017

OTHER PUBLICATIONS

Peng, Yu, et al. "IDBA—a practical iterative de Bruijn graph de novo assembler." Research in Computational Molecular Biology: 14th Annual International Conference, RECOMB 2010, Lisbon, Portugal, Apr. 25-28, 2010. Proceedings 14. Springer Berlin Heidelberg, 2010. (Year: 2010).*

Liao, Yu-Chieh, et al. "MyPro: A seamless pipeline for automated prokaryotic genome assembly and annotation." Journal of microbiological methods 113 (2015): 72-74. (Year: 2015).*

"GitHub—tseemann/VelvetOptimiser: Automatically optimise three of Velvet's assembly parameters" webpage <github.com/tseemann/VelvetOptimiser>, Jul. 17, 2017, retrieved from the Internet Archive Wayback Machine <web.archive.org/web/20170721160537/https://github.com/tseemann/VelvetOptimiser> on May 26, 2023 (Year: 2017).*

Bankevich et al., "SPAdes: A New Genome Assembly Algorithm and Its Applications to Single-Cell Sequencing," Journal of Computational Biology, vol. 19, No. 5, 2012.

Bradnam et al., "Assemblathon 2: evaluating de novo methods of genome assembly in three vertebrate species," GigaScience 2(1): 10 • Jul. 2013+AS2:AS18.

Cha et al., "Optimizing k-mer size using a variant grid search to enhance de novo genome assembly," BioInformation 12(2): 36-40 (2016).

Chikhi et al., "Informed and automated k-mer size selection for genome assembly," Bioinformatics, vol. 30, No. 1, 2014, pp. 31-37.

Chikhi et al., "Space-Efficient and Exact de Bruijn Graph Representation Based on a Bloom Filter," Algorithms in Bioinformatics, B. Raphael and J. Tang (Eds.): WABI 2012, LNBI 7534, pp. 236-248, 2012; copyright Springer-Verlag Berlin Heidelberg 2012.

Durai et al., "Informed kmer selection for de novo transcriptome assembly," Bioinformatics, 32(11), 2016, 1670-1677.

Ekblom et al., "A field guide to whole-genome sequencing, assembly and annotation," Evolutionary Applications 7(9) Jun. 2014, pp. 1026-1042.

Georganas et al., "HipMer: An Extreme-Scale De Novo Genome Assembler," Conference paper: the International Conference for High Performance Computing, Networking, Storage and Analysis; Nov. 2015.

Kim et al., "K-mer clustering algorithm using a MapReduce framework: application to the parallelization of the Inchworm module of Trinity,". BMC Bioinformatics (2017) 18:467.

Li et al., "MEGAHIT: an ultra-fast single-node solution for large and complex metagenomics assembly via succinct de Bruijn graph," Bioinformatics, 31(10), (2015), 1674-1676.

Li et al., "Optimizing Spaced k-mer Neighbors for Efficient Filtration in Protein Similarity Search," IEEE/ACM Transactions On Computational Biology and Bioinformatics, vol. 11, No. 2, Mar./Apr. 2014, pp. 398-406.

Mahadik et al., "Scalable Genomic Assembly through Parallel de Bruijn Graph Construction for Multiple K-mers," Proceedings of ACM BCB, Aug. 2017, Boston, MA; copyright 2017 ACM.

Miller et al., "Assembly algorithms for next-generation sequencing data," Genomics 95 (2010) 315-327.

Safanova et al., "dipSPAdes: Assembler for Highly Polymorphic Diploid Genomes," Journal of Computational Biology, vol. 22, No. 6, 2015; pp. 528-545.

Shariat et al., "HyDA-Vista: towards optimal guided selection of k-mer size for sequence assembly," BMC Genomics 2014, 15(Suppl 10):S9.

Simpson et al., "ABySS: A parallel assembler for short read sequence data," Genome Res. Jun. 2009; 19(6): 1117-1123.

Wu et al., "TIGER: tiled iterative genome assembler," BMC Bioinformatics 2012, 13(Suppl 19):S18.

* cited by examiner

METHODS OF OPTIMIZING GENOME ASSEMBLY PARAMETERS

BACKGROUND

The present invention relates to methods of optimizing genome assembly parameters, more specifically to machine learning methods of optimizing genome assembly parameters.

Decreased cost and increased accessibility of high-throughput sequencing have led to a rapid increase in numbers of sequenced bacterial genomes. The number of sources of genome projects has also increased dramatically. This massive growth of available bacterial genomic data has great potential, but the utility of the data depends on their quality. Many methods of genomic assembly have been developed, but de novo assembly of bacterial genomes is a multivariable process that remains non-standardized.

The most commonly used de novo genome assembly algorithms for bacterial genomic data utilize de Bruijn graphs, a representation that requires the sequence data to be broken down into k-mers of uniform length. The choice of k-mer size is critical for de novo genome assembly. In addition, the assembly itself should be self-consistent. Small k-mer sizes can inhibit the resolution of repeat sequences, creating a greater number of ambiguities in the assembly. On the other hand, large k-mer sizes can be sensitive to sequencing errors, heterozygosity, and low coverage. Large k-mer sizes can also result in a greater number of short contigs, and can prevent assembly entirely.

Some existing methods for genome assembly that use de Bruijn graphs rely on breaking nucleotide sequence data into k-mers, and many of these methods use a range of k-mer sizes (e.g., SPAdes, ABySS, Minia, and MegaHit). Other methods attempt to determine the optimal k-mer size using strategies such as homology-based k-mer size prediction or the number of distinct genomic k-mers.

More efficient methods are needed for determining an optimal k-mer size, or range of k-mer sizes, for a given genome assembly that are adaptable to machine learning.

SUMMARY

Accordingly, a method is disclosed comprising:
  selecting a k-mer-based de novo genome assembler program, designated assembler;
  providing a set of parameters for assembly of a set of sequenced nucleic acids, the parameters having respective values and respective priority scores, the parameters including a k-mer parameter having an initial length k in number of nucleotides, k being a positive integer equal to at least 35;
  providing a set of quality metrics for assembly of a set of sequenced nucleic acids, the quality metrics having respective weights indicating importance, respective target values, and respective computed values calculated during assembly, a given quality metric depending on one or more of the parameters;
  initiating assembly of the set of sequenced nucleic acids by the assembler, the assembler utilizing the set of parameters and the set of quality metrics, thereby forming intermediate assembled sequences;
  performing a procedure iteratively until the respective computed values of the quality metrics equal the respective target values, the procedure comprising the steps of: i) stopping the assembler when the respective computed values of the quality metrics do not equal the respective target values, ii) modifying at least one of the parameters and/or at least one of the quality metrics, iii) deleting any intermediate assembled sequences, iv) initiating assembly of the set of sequenced nucleic acids by the assembler, and v) calculating values of the quality metrics including any modified quality metrics, the procedure terminating while utilizing a set of final parameters and a set of final quality metrics, the final parameters including a final k-mer parameter of length k'; and
  completing assembly of the set of sequenced nucleic acids using the assembler, the set of final parameters, and the set of final quality metrics, thereby forming one or more final assembled genomes.

Also disclosed is a system comprising one or more computer processor circuits configured and arranged to:
  select a k-mer-based de novo genome assembler program, designated assembler;
  provide a set of parameters for assembly of a set of sequenced nucleic acids, the parameters having respective values and respective priority scores, the parameters including a k-mer parameter having an initial length k in number of nucleotides, k being a positive integer equal to at least 35;
  provide a set of quality metrics for assembly of a set of sequenced nucleic acids, the quality metrics having respective weights indicating importance, respective target values, and respective computed values calculated during assembly, a given quality metric depending on one or more of the parameters;
  initiate assembly of the set of sequenced nucleic acids by the assembler, the assembler utilizing the set of parameters and the set of quality metrics, thereby forming intermediate assembled sequences;
  perform a procedure iteratively until the respective computed values of the quality metrics equal the respective target values, the procedure comprising the steps of: i) stopping the assembler when the respective computed values of the quality metrics do not equal the respective target values, ii) modifying at least one of the parameters and/or at least one of the quality metrics, iii) deleting any intermediate assembled sequences, iv) initiating assembly of the set of sequenced nucleic acids by the assembler, and v) calculating values of the quality metrics including any modified quality metrics, the procedure terminating while utilizing a set of final parameters and a set of final quality metrics, the final parameters including a final k-mer parameter of length k'; and
  complete assembly of the set of sequenced nucleic acids using the assembler, the set of final parameters, and the set of final quality metrics, thereby forming one or more final assembled genomes.

Further disclosed is a computer program product, comprising a computer readable hardware storage device having a computer-readable program code stored therein, said program code configured to be executed by a processor of a computer system to implement a method comprising:
  selecting a k-mer-based de novo genome assembler program, designated assembler;
  providing a set of parameters for assembly of a set of sequenced nucleic acids, the parameters having respective values and respective priority scores, the parameters including a k-mer parameter having an initial length k in number of nucleotides, k being a positive integer equal to at least 35;

providing a set of quality metrics for assembly of a set of sequenced nucleic acids, the quality metrics having respective weights indicating importance, respective target values, and respective computed values calculated during assembly, a given quality metric depending on one or more of the parameters;

initiating assembly of the set of sequenced nucleic acids by the assembler, the assembler utilizing the set of parameters and the set of quality metrics, thereby forming intermediate assembled sequences;

performing a procedure iteratively until the respective computed values of the quality metrics equal the respective target values, the procedure comprising the steps of: i) stopping the assembler when the respective computed values of the quality metrics do not equal the respective target values, ii) modifying at least one of the parameters and/or at least one of the quality metrics, iii) deleting any intermediate assembled sequences, iv) initiating assembly of the set of sequenced nucleic acids by the assembler, and v) calculating values of the quality metrics including any modified quality metrics, the procedure terminating while utilizing a set of final parameters and a set of final quality metrics, the final parameters including a final k-mer parameter of length $k^t$; and completing assembly of the set of sequenced nucleic acids using the assembler, the set of final parameters, and the set of final quality metrics, thereby forming one or more final assembled genomes.

Also disclosed is a method of genome assembly for single assembly or sets of assemblies by optimizing the k-mer length parameter, the method comprising the following steps:

using high throughput sequencing to sequence one or more genomes, thereby forming sequence data;

processing the sequence data for quality control;

selecting a quality metric for assembly of the sequence data, the quality metric having a calculated value during an assembly and a target value;

initiating assembly of the sequence data using a set of k-mer values for the one or more genomes, the k-mer values having scores and ranks;

performing a procedure during the assembly when the calculated value of the quality metric does not equal to the target value, the procedure comprising:
  a) deleting any intermediate assembled sequences,
  b) modifying the k-mer values,
  c) initiating assembly using the modified k-mer values,
  d) assessing the calculated value of the quality metric relative to the target value before the assembly is complete;
  e) updating the scores and ranks of the k-mer values;

repeating the procedure until the calculated value of the quality metric equals the target value; and completing the assembly.

The above-described and other features and advantages of the present invention will be appreciated and understood by those skilled in the art from the following detailed description, drawings, and appended claims.

DETAILED DESCRIPTION

Figure 1:
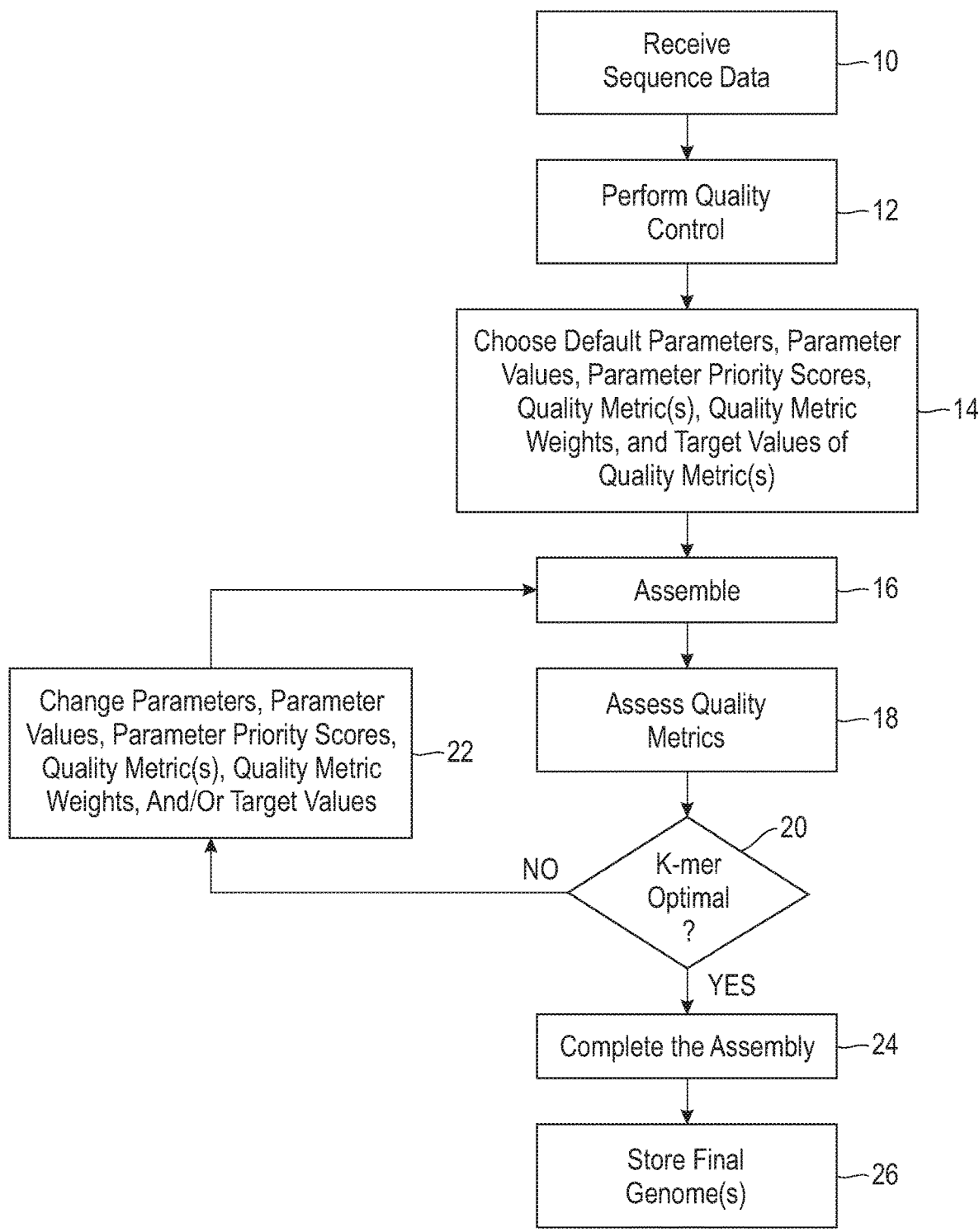
FIG. 1 is a flow diagram illustrating the disclosed method of optimizing parameters used by a de novo assembler of sequence data.

A method is described for iteratively modifying and optimizing k-mer length and other key parameters used in a genome assembly process. The method is unbiased and scalable to a large number of genomes without prior knowledge of the optimal length of k-mer size as a unique input for any given genome assembly. This is crucial since many applications require self-consistent assembly parameters. The method utilizes one or more pre-chosen quality metrics, and iteratively modifies the k-mer length and/or other assembly parameters to determine which k-mer lengths provide the best value of the metric(s) (i.e., a value of the metric that ensures a self-consistent result). The number of optimized k-mer lengths can be a positive whole number between 1 and 1000. The method can determine a list of optimal k-mer sizes for assembly of one or more genomes. That is, the k-mer size can be optimized for a single genome or a collection of genomes (e.g., hundreds of thousands or more genomes).

Definitions

The following definitions are applicable.

Abbreviations A, C, G, and T refer to nucleotide bases adenine, cytosine, guanine, and thymine, respectively.

A "clade" is a group of biological taxa (such as species) that includes all descendants of one common ancestor.

A "contig" is a set of overlapping DNA sequences that together represent a consensus sequence of DNA or a region thereof.

A "consensus sequence" is the calculated order of the most frequent residues found at each position in a sequence alignment.

"Copy number" means the number of copies of a gene or plasmid within a genome. The copy number can vary from individual to individual.

"Coverage" or "depth of coverage" is the number of times a given sequence from a genome is represented in the set of sequences derived from that genome.

A De Brujin Graph is a directed graph that represents overlaps between sequences.

De novo genome assembly is a process of genome assembly without a reference sequence to guide the assembly process.

"DNA" is deoxyribonucleic acid.

A "protein domain" is a region of a protein having a particular shape and/or function.

A "gene" is the basic unit of heredity, a linear sequence of nucleotides along a segment of DNA that provides the coded instructions for synthesis of RNA, which, when translated into protein, leads to the expression of a hereditary trait.

"Genetic distance" is a quantitative measure of the divergence of one or more regions of DNA and/or RNA between species or populations of species. Genetic distance can be based on whole genome-whole genome distances, gene-gene distances, protein domain-protein domain distances (i.e., the portions of the DNA encoding for a particular protein domain), protein-protein distances (i.e., the portions of the DNA encoding for a whole protein), or protein domain-protein domain distances based on an amino acid distance metric. More specifically, genetic distance is a measure of the differences in nucleotide sequences of the k-mers with respect to whole genomes, genes, and/or other genetic regions of interest. Thus, the average number of codon or nucleotide differences per gene can be a measure of genetic distance. For the present work, the genetic distance is a numeric distance calculated between each pair of genomes of the reference database using MASH (which utilizes the MinHash algorithm). The MinHash algorithm calculates distance from a Jaccard index. The Jaccard index is calculated from "sketches" of the k-mers, which are diagrams showing the similarity and differences between k-mers of the pair of genomes.

A "genome" is the total genetic content of an organism. In the case of bacteria, the genome is DNA.

"Genome assembly" is a process of aligning and merging a set of sequence fragments that were derived from a larger genome in order to reconstruct the original sequence.

A "ground truth dataset" is a dataset formed by direct observation (measured data) as opposed to data obtained by inference or assumption.

Herein "high-throughput sequencing" (HTS) is any method of sequencing a nucleic acid that is highly parallel and does not involve cloning the nucleic acid. A genome or metagenome is cut into a large number of fragments, and the fragments are sequenced in parallel.

"Homology" refers to the similarity of sequences (e.g., DNA, RNA, Protein, etc.) arising from a common ancestry.

"Hybridization" is the formation of double-stranded helix from single-stranded complimentary pairs of DNA and/or RNA by annealing.

The term "k-mer" means a sub-sequence of a read obtained through DNA sequencing having length k in number of nucleotide base units, where k is a positive whole number greater than 1.

Herein, a "database" is an electronic file for storing and retrieving data. Databases are also referred to herein as data tables. Data tables comprise rows and columns (i.e., fields) of data. The rows are formally called tuples or records. A data table comprises one or more records, each record comprising one or more defined fields having respective defined data types (e.g., text, numeric, date, time, memo, and so on) and defined field lengths where applicable. A working data table comprises at least one record containing data in one or more fields of the record. The data tables are located on data storage devices, which can be remote or local relative to the user input/output devices. A "database system" comprises at least one data table and a database management software program for managing the storage and retrieval of data to and from the data tables. The database management programs can be remote or local relative to the data tables and/or the end user. A Relational Database Management System (RDBMS) is a database management system (DBMS) that uses relational techniques for storing and retrieving data using data tables. A relational database system can have many data tables, and each data table can have multiple records and multiple fields within each record. A data table in a relational database system can be accessed using an index. An index is an ordered set of references (e.g., pointers) to the records or rows in a data table. The index is used to access each record in the file using a key (e.g., one or more of the fields of the record or attributes of the row). Without an index, finding information in a large data table would require a resource-intensive time-consuming scan (e.g., linearly) of each record of a table. Indexes provide a faster alternate technique of accessing data contained in one or more data tables that are linked by a common key. Users can create indexes on a table after the table is built. An index is based on one or more columns (fields) of a given table.

A "k-mer database" is a database in which a given record comprises a field for storing a k-mer of a nucleic acid sequence of one or more organisms. Another field of the record stores a taxonomic ID, a set of taxonomic IDs, or a taxonomic ID that associates the k-mer to a lowest common ancestor node (LCA) of a taxonomic tree. As will be described below in more detail, other fields of the record can store reference IDs to a reference taxonomy. Still other fields of the record can store metadata associated with the k-mer and/or the nucleic acid sequence from which the k-mer originated.

Kraken is a taxonomic classifier that assigns taxonomic labels to DNA sequences, including k-mers. Kraken uses k-mers from a sequence read to query a reference database containing k-mers from reference genomes (i.e., the genomes of RefSeq Complete at NCBI) for matches. The k-mers are mapped to the lowest common ancestor (LCA) of all genomes known to contain a given k-mer. Typically, the k value for a k-mer query is 31 but this value can be modified by the user. For typical queries, k can be a positive whole number in the range of about 10 to about 1000.

Herein, a "Kraken database" is an electronic file containing k-mers assigned to a taxonomic hierarchy by the Kraken classifier.

"L50" is a count defined as the smallest number of contigs whose length sum makes up half of genome size. Given a set of contigs, calculate the N50 (see below). The L50 is the number of contigs whose summed length is N50.

"LA50" is a count calculated as follows. Given a set of contigs, calculate the NA50 (see below). The LA50 is the count of the number of blocks that are the same or greater length than the NA50.

"LG50" is a count calculated as follows. Given a set of contigs, calculate the NG50 (see below). The LG50 is the count of the number of contigs that are the same or greater length than the NG50.

"LGA50" is a count calculated as follows. Given a set of contigs, calculate the NGA50 (see below). The LGA50 is the count of the number of blocks that are the same or greater length than the NGA50.

A "locus" (plural loci) is a position on a genome (e.g., gene, regulatory element, origin of replication).

A "metagenome" is all the genetic information of a sample.

"Metagenomics" is the analysis or study of metagenomes.

"Metatranscriptome" is the collection of all RNA transcripts of a sample.

"Metatranscriptomics" is the analysis or study of metatranscriptomes.

A "microbiome" is a community of microorganisms that inhabit a particular environment (e.g., microbes of the human gut), or a sample taken therefrom.

A "misassemble" is an incorrectly assembled contig or genome that contains an insertion, deletion, inversion, or rearrangement that is the result of decisions made by the assembly program.

"N50" is a length in nucleotide base units calculated as follows. Given a set of contigs, the length of each and the length of the sum of the set are calculated. The contigs are ordered by length and the accumulated length from the largest contig to the smallest is calculated. The N50 is the shortest sequence length at the accumulation of 50% of the sum of the set of contigs. N50 can also be thought of as the length of the contig for which the number of bases from all contigs longer and including it will be as close as possible to the number of bases from all contigs shorter than it.

"NA50" is a length in nucleotide base units computed in two steps. First, contigs are aligned to a reference. Contigs are then broken into multiple blocks at misassembly breakpoints and at unaligned regions within a contig. The NA50 is calculated like the N50 using the blocks instead of the contigs.

"NG50" is a length in nucleotide base units similar to N50, but uses estimated genome size (usually by using the size of a reference genome) instead of the length of the sum of the set of contigs. Given a set of contigs, the length of each is calculated. The contigs are ordered by length. The accumulated length from the largest contig to the smallest is calculated. The NG50 is the shortest sequence length at the accumulation of 50% of estimated genome size.

"NGA50" is a length in nucleotide base units similar to NG50 and NA50. The contigs are broken into blocks as in the NA50. The NGA50 is calculated like the NG50 using the blocks.

"Origin of replication" is the locus at which DNA replication begins.

Operational taxonomic units (OTUs) are used by taxonomy classifier systems (e.g., Kraken classifier) to categorize the k-mers based on sequence similarity. For example, in 16S rRNA metagenomics, OTUs are clusters of similar sequence variants of the bacterial 16S rRNA marker gene sequence. Each cluster represents a taxonomic unit of a bacterial species or genus depending on the sequence similarity threshold. Typically, OTU clusters are defined by a 97% identity threshold of the 16S gene sequences to distinguish bacteria at the genus level. Species separation requires a higher threshold of 98% or 99% sequence identity, or the use of exact sequence variants instead of OTU cluster.

"Paired-end sequencing" refers to sequencing from both ends of a DNA fragment.

A "plasmid" is a self-replicating extrachromosomal circular DNA that replicates independently of the bacterial chromosome and carries genes for functions not essential for growth.

"RNA" is ribonucleic acid.

"mRNA" refers to messenger RNA. The mRNA codes for amino acid sequences composing proteins.

"rRNA" refers to ribosomal RNA.

"tRNA" refers to transfer RNA. A tRNA transports a specific amino acid to a ribosome for synthesis of a protein.

An "RNA transcript" is an RNA produced through the process of transcription of DNA.

"Sample" means any sample containing DNA and/or RNA capable of undergoing analysis using the disclosed methods.

A "scaffold" is a reconstructed portion of a whole genome containing two or more contigs of known base order separated by gaps of unknown base order.

"Sequencing" refers to a process of determining the precise order of base residues (i.e., nucleotides) in a nucleic acid (e.g., DNA, RNA).

A "sequence" is a fragment of a nucleic acid (e.g., RNA, DNA) that has been sequenced (i.e., the order of the nucleotide bases is known).

A "sequence read" or "read" is a finite length or fragment of a nucleic acid that is output by a sequencing instrument in the form of text strings of the nucleotide base units. For example, a read from an Illumina sequencer is currently 100-150 base pairs in length. Sequencing may also be done on "paired end" reads where two reads are connected by a spacer (that is not read), increasing the effective read length to 300 or more and covering a larger region of the genome.

A "sequence alignment" is a way of arranging sequences to identify regions of similarity, which may be a consequence of functional, structural, or evolutionary relationships between the sequences.

"Shotgun sequencing" is a quasi-random process in which a nucleic acid is broken up into many random smaller fragments that are individually sequenced. The sequences are ordered based on overlapping regions of genetic code and reassembled into the complete sequence of the nucleic acid.

"Taxonomy" is a biological scheme of classification of organisms.

"Taxonomic rank" is the relative level of a(n) organism/group of organisms in a taxonomic hierarchy. Herein, for bacteria, the heirarchy is domain, kingdom, division, phylum, class, order, family, genus, species, sub-species, and strain. Each of the foregoing classifications is a "rank" on the taxonomic tree.

A "taxonomic tree" herein is a data structure for classifying organisms. The taxonomic tree comprises nodes (i.e., taxa, singular taxon) that are grouped into "parent nodes" linked to "child nodes". Parent nodes are depicted above child nodes in the tree diagram. Child nodes are taxonomic descendants of parent nodes. For example, a genus (parent node) can be linked to two or more species (child nodes). The taxonomic tree can be rooted (i.e., known ancestral root) or unrooted (i.e., unknown ancestral root), bifurcating (i.e., two child nodes per parent node) or multi-furcating (i.e., more than two child nodes per parent node). Typically, the taxonomic tree is in the form of a "binary tree" (i.e., each parent node has two child nodes). A "leaf node" is a child node having no descendants (e.g., the species of a genus). In the self-consistent taxonomy, each leaf node has one genome. "Internal nodes" are all nodes other than the leaf nodes.

"Transcription" is the process of forming an RNA from a DNA template.

The abbreviation "bp" means "base-pair" (e.g., a read of 100-bp means that one DNA read has 100 nucleotides in the polymer chain.

"Miscalling" refers to a sequencing error where a nucleotide in a sequence read is different from the true nucleotide.

A quality value is an assigned value given to each nucleotide in a sequence read that reflects the likelihood of miscalling the nucleotide. The higher the quality value is, the lower the likelihood of miscalling.

A "reference genome" is a genome from the same species or close species that has already been sequenced.

"Mapping" a sequence read is a process of finding the position or coordinate of a sequence read on the reference genome.

A "perfect match prefix" is a k-mer of a sequence read that is identical to, or a perfect match to, some equal-length k-mer(s) of the reference genome. The k-mer of the sequence read is used to initially anchor the sequence read on the reference genome.

"Base substitution" is a term describing certain bases of a sequence read differing from the corresponding bases of a reference genome after the sequence read is mapped to the reference genome.

"Base insertion" occurs when some continuous bases are inserted between two adjacent bases on a sequence read compared with the reference genome.

"Base deletion" occurs when a sequence read loses some continuous bases compared with the reference genome.

"INDEL" is an insertion or deletion in a read when trying to find the best alignment of a read to a reference genome.

The method is illustrated in the flow diagram of FIG. 1 beginning with a set of sequenced nucleic acids (10). Bacterial SRA Datasets that were at least 100 MB of size were downloaded from NCBI's Sequence Read Archive (SRA) file transfer protocol (FTP) site (see the website given by the concatenation of "ftp://ftp.ncbi.nlm" and ".nih.gov/sra/"). These datasets were converted to FASTQ format using SRA-tools. Genomes were assembled using the methods as described in the invention. The sequenced nucleic acids can originate from a working sample containing one or more microorganisms (i.e., medical sample, environmental sample, food sample) whose nucleic acids have been subjected to high throughput sequencing.

The resulting sequencing reads generated from a sequencing method are referred to herein as raw sequences or raw reads. A given raw sequence can have a length of 35 nucleotides (nt) or more, 250 nt or more, 35 nt to about 100,000,000 nt, 35 nt to about 1,000,000 nt, or more preferably 35 nt to 1000 nt.

Quality control is performed on the sequenced nucleic acids (12). Quality control can include, for example, the removal (trimming) of low-quality reads or segments of reads. Non-limiting trimming algorithms and software programs for cleanup of raw DNA sequence reads include SolexaQA DynamicTrim, FASTX-ToolKit, ConDeTri, NGS QC Toolkit, FASTQC, and Trimmamatic. For the present work, FASTQC and Trimmamatic were used on the genomes of the sample. The result was a "clean sample" containing 170,000 assembled genomes.

The resulting sequencing reads generated from the quality control process are referred to herein as clean sequences or clean reads. A given clean sequence can have a length of 35 nucleotides (nt) or more, 250 nt or more, 35 nt to about 100,000,000 nt, 35 nt to about 1,000,000 nt, or more preferably 35 nt to 1000 nt.

An initial set (default set) of quality metrics is chosen for the assembly, as well as an initial set of assembly parameters (e.g., k-mer value), on which the quality metrics depend. The quality metrics are assigned respective "desirable values" (i.e., target values). The target values can be assigned programmatically or manually, preferably programmatically. The target values can be qualitative (e.g., pass/fail, true/false) or quantitative (e.g., a number). Quantitative target values can be one number or a range of numbers. A quality metric can be chosen which represents an average of one or more other quality metrics.

More specifically, let $M_i$ be the value of ith quality metric and $w_i$ be the relative weight or importance of that metric, where i is a whole number integer greater than or equal to 0. The value $M_i$ is a function $m_i$ of the k-mer length k and other assembly parameters, where length k is a positive whole number greater than 0. $M_i$ is then expressed as equation (1).

$$M_i = m_i(k) \quad (1)$$

An objective function F(k) representing the overall quality to be optimized for a set of size N quality metrics is then expressed as equation (2):

$$F(k) = \sum_{i=0}^{N} m_i(k) w_i \quad (2),$$

where N is a positive whole number greater than or equal to 1, and $w_i$ is the weight or importance of the ith quality metric $m_i(k)$, where $w_i$ is a number greater than 0.

The value $M_i$ of the function $m_i(k)$ depends on the priority scores of the parameters on which $m_i(k)$ depends. A priority score is assigned to each of the parameters of $m_i(k)$ to establish the order in which the parameters are evaluated and the weight or importance of the parameter when calculating the value of $m_i(k)$. A parameter can have a priority score in the range of 1 to 100, or alternatively 0 to 1. For a given quality metric, the parameters of the given quality metric are ranked according to priority score and evaluated starting with the highest priority parameter first and moving toward the lowest priority parameter. If the computed value of $m_i(k)$ is not a desirable value before the lowest priority parameter of $m_i(k)$ is evaluated, the computation of the value of $m_i(k)$ can be interrupted and the assembly stopped. If interrupted, one or more of the parameters, the value of the parameters, the priority order of the parameters, the quality metrics, and the target values of the quality metrics can be modified before re-initiating assembly.

For any given optimization criteria, the k-mer parameter of initial length k can be optimized iteratively for the assembly of a single genome or for the collective properties of a set of genomes that must be assembled using a common assembly process (e.g., with a common k-mer length). For example, when creating a library of genomes for a particular species or genus, the genomes should be assembled with a self-consistent process so they may be later used to measure genome-genome distance for outbreak detection, source tracking, and other uses. In this case, the k-mer length can be selected to minimize or maximize the average of one or more quality metrics.

The above is summarized in block (14) of FIG. 1, where parameters, parameter values, parameter priority scores, quality metrics, quality metric weights, and target values of the quality metrics are chosen prior to initiating assembly.

The assembly is initiated (16) with the default set of assembly parameters and quality metrics using a selected k-mer based de novo assembler. The assembler preferably utilizes de Bruijn graphs (DBGs). Non-limiting de novo assemblers utilizing DBGs include EULER, Velvet, ABySS, SPAdes, Minia, Trinity, MEGAHIT, SGA, PCAP, NA, SOAPdenovo, Newbler, Newbler/CABOG, ARACHNE, Ray, Phusion assembler/ABySS, Celera Assembler, CLC bio Assembler, ALLPATHS-LG, Newbler/Bowtie, Newbler, CLC/SSPACE, and Newbler/SOAPdenovo.

The assembly generates intermediate assembled sequences from the set of clean reads. The intermediate assembled sequences can be partial or fully assembled genomes. To conserve processing time, the quality metrics are preferably evaluated at an intermediate stage of the assembly before obtaining a complete genome or set of genomes.

The output of the assembly is analyzed (18) using an iterative procedure that evaluates the computed values of one or more of the quality metrics. In the non-limiting example of FIG. 1, the k-mer length is found to be non-optimal (20) based on an assessed quality metric(s) of the assembly.

In the iterative procedure, when the calculated values of the quality metrics do not equal the target values, the assembly is stopped. One or more of the assembly parameters, parameter priority scores, parameter values, quality metrics, quality metric weights, and/or quality metric target values are then modified (22). An initial assembly parameter other than the k-mer length can be deleted, and/or new assembly parameters can be added along with their corresponding initial values and priority scores. When revisions are complete, previously generated intermediate assembled sequences are deleted and the assembly is re-initiated using the modified set of parameters and/or modified quality metrics (16). Sequential revisions of the parameters and/or quality metrics can be saved and stored for comparison. The steps of (16)-(22) are then repeated until the calculated values of the quality metrics equal the target values of the quality metrics. The iterative procedure terminates during an assembly using the most recently modified set of parameters and quality metrics, which are referred to as the set of final parameters (optimized parameters) and set of final quality metrics (optimized quality metrics). If the iterative procedure terminates before assembly is complete, the assembly is completed (24) using the set of optimized parameters and set of optimized quality metrics, resulting in one or more final assembled genomes. Alternatively, a new complete de novo assembly can be performed uninterrupted with the set of sequenced nucleic acids using the set of optimized parameters and set of optimized quality metrics with the assembler. The final assembled genomes are then stored (26). Preferably, the set of optimized parameters including parameter values, parameter priority scores, and rankings, and set of optimized quality metrics including quality metric values, and quality metric weights are stored with the final assembled genomes.

Figure 2:
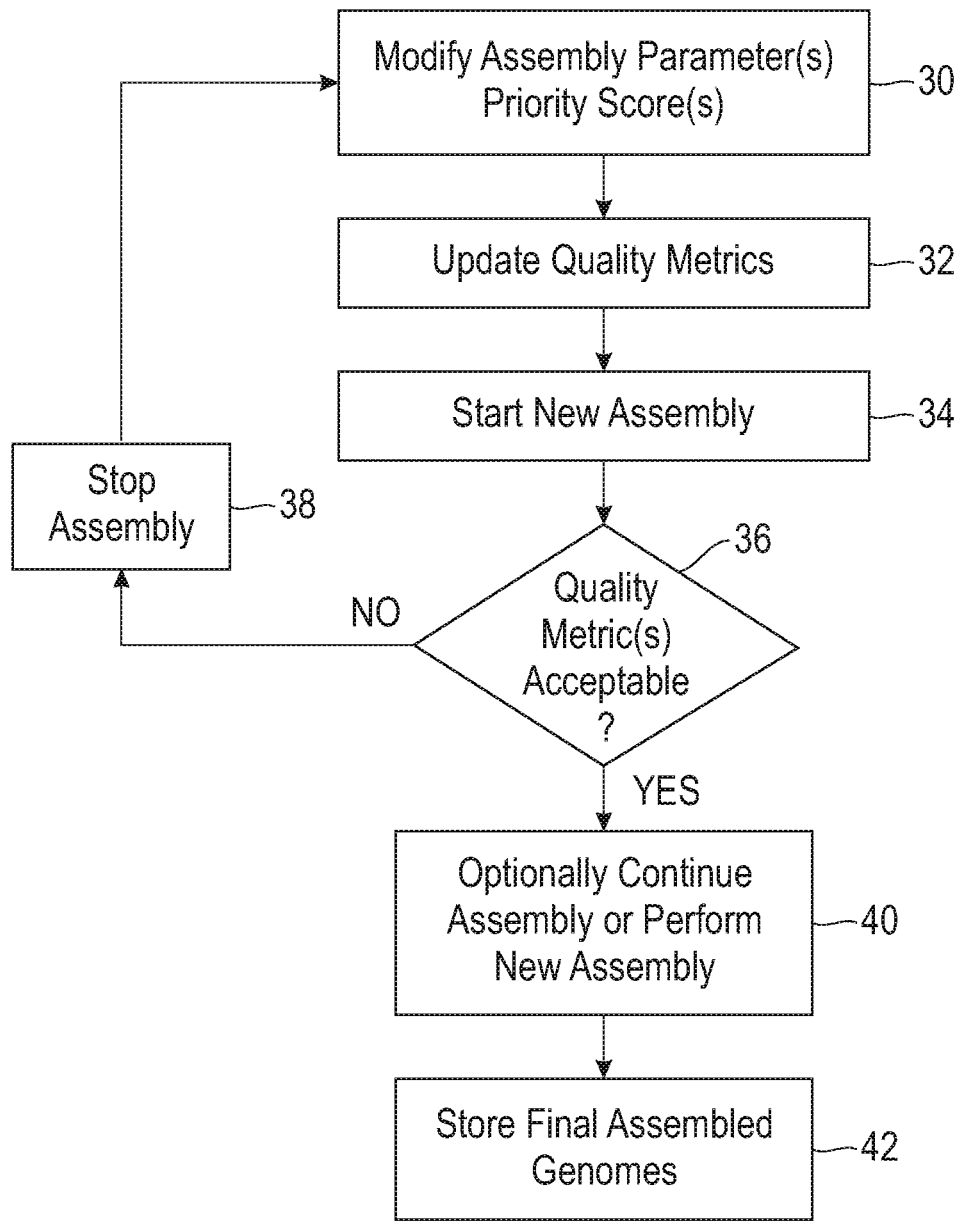
FIG. 2 is a flow diagram providing more details of the iterative loop in the optimization process of the parameters.

The iterative procedure of steps (16)-(22) is further detailed in the flowchart of FIG. 2, which shows a process that can be used by a computer program to automatically optimize parameters and quality metrics. In a first step, the computer program can modify zero or more of the parameters (30). Parameters other than the k-mer parameter can be deleted. Modifying a given parameter includes changing the given parameter value and/or changing the given parameter priority score. The quality metrics are then modified using the modified parameters, if any (32). The quality metrics can also be modified by changing the rankings of the parameters based on changes in parameter priority score and/or modifying the weight of a given quality metric (see Equation (2)). Deleting a parameter can also result in deleting a quality metric, thus modifying the set of quality metrics. The modified parameters and/or modified quality metrics are then applied in a new assembly (34). The assembly process computes the value of each quality metric starting with the higher ranked assembly parameters and moving to the lower ranked assembly parameters. The assembly can be interrupted at different stages to assess the one or more of the quality metrics. Alternatively, the quality metrics can be assessed in a parallel process without interrupting the assembly. The assessment of the quality metric(s) can be conducted on a partially assembled or wholly assembled genome or set of genomes. If the value(s) of the quality metric(s) are found unsuitable (36) (i.e., failing to meet target values, outside desired ranges, and so on), the assembly stops (38). Steps (30)-(38) are repeated until the quality metrics are acceptable (equal to target values). If acceptable, the iterative procedure stops while using the most recent set of parameters and set of quality metrics, designated final parameters and final quality metrics, which are also referred to herein as the set of optimized parameters and set of optimized quality metrics. The assembly can be continued to completion if it is not already complete by using the set of optimized parameters and the set of optimized quality metrics, or a new assembly can be performed uninterrupted using the set of optimized parameters and the set of optimized quality metrics (40) with the assembler, thereby forming one or more final assembled genomes. The final assembled genomes are then stored (42), preferably with the set of optimized parameters including parameter values, parameter priority scores, and parameter rankings, and with the set of optimized quality metrics including calculated values, target values, and weights.

This method provides a procedure to test values of assembly parameters during assembly and more efficiently operate an assembly process. The method is adaptable to machine learning. Output assembly statistics can be used to guide the optimal set of one or more assembly parameters without input from the user and automatically create an optimized parameter value list for a given set of genome sequences.

Quality Metrics

Non-limiting quality metrics include N50, NA50, NG50, NGA50, L50, LA50, LG50, LGA50, number of contigs, number of contigs above a given size, number of edges or connections between contigs, genome size, the difference between the mean or median assembled genome sizes and the mean or median sizes of reference genomes of a given taxonomic rank (e.g., species, genus), the difference between the standard deviation of the sizes of the assembled genomes and the standard deviation of the reference genomes of a given taxonomic rank, the number of misassembles, the coverage of the assembly (e.g., per base, per contig, and/or per assembly), and the "composition" of the assembly (e.g., the relative abundance of each base, the repetitive content of the genome). In an embodiment, the assembly includes a quality metric for the difference between the standard deviation of the sizes of the intermediate assembled sequences and the standard deviation of the sizes of reference genomes.

The quality metrics can be used singularly (e.g., number of contigs less than 50 nt in length OR genome size greater than 100 megabytes OR coverage (depth) greater than $10^8$). Alternatively, the quality metrics can be used in combination (e.g., number of contigs less than 50 nt in length AND genome size greater than 100 megabytes AND coverage (depth) greater than $10^8$).

Assembly Parameters

The assembly parameters can be any configurable parameter for a genome assembler. Non-limiting assembly parameters include k-mer length, read length, coverage cutoff value, mismatches allowed, expected genome size, insert size, taxonomic rank, sequencing error rate expectation, sequencer type, sequencing strategy, specific sequencer machine type, strategy of library creation, and sample supplier).

One or more of the parameters can have the highest importance (i.e., priority score), usually the k-mer parameter. Optionally, the assembly can be performed with another parameter having greater importance than the k-mer parameter (e.g., coverage cutoff value, number of mismatches allowed, expected genome size, insert size, or sequencing error rate expectation).

Preferably, the set of optimized parameters (final parameters) generated by the disclosed iterative process are stored with the final assembled genome(s). Stored parameters can be selectively used to constrain future assemblies, thereby reducing the number of assemblies required to form an set of optimized parameters, minimizing the set of assembly parameters needed to obtain a high quality final assembled genome, and/or achieve an overall assembly quality of a prior final assembled genome. The stored parameters and/or scores can be applied to another set of genome data for a quick assembly.

The final assembled genomes can contain metadata (e.g., sequencer type, specific sequencing machine type, strategy of library creation, sample supplier of raw data, taxonomic rank, predicted genome size) associated with stored parameters that can be used to constrain the stored parameters in future assemblies. For example, the metadata can contain a specific sequencer type used to generate the raw sequences. The stored parameters can then be constrained to raw data sets generated using the specific sequencer type.

K-Mer Length Optimizations

The k-mer length can be optimized for a single genome or a set of multiple genomes. When optimized for multiple genomes, the optimization can be based on an average of the quality metric(s) used. Alternatively, the k-mer length can be optimized for a subset of the final assembled genomes, where the subset comprises more than one final assembled genome. The subsets can be defined by organism taxonomic rank (e.g., optimization by species, by genus, by strain, etc.), by sequencing technology (e.g., Illumina, PacBio, etc.), or a combination thereof. The final k-mer value k' can be an average of k-mer values used in the iterative procedure.

Sequencing

Non-limiting methods of DNA/RNA sequencing include massively parallel signature sequencing (or MPSS), Polony sequencing, Roche 454 pyrosequencing method, ION TORRENT™ (Life Technologies Corporation, corporation of Delaware, U.S.), ILLUMINA™ sequencing (Illumina, Inc., a corporation of Delaware, U.S., formerly Solexa sequencing), sequencing by oligonucleotide ligation and detection (SOLiD) by Life Technologies Corporation, PacBio™ sequencing (Pacific Biosciences of California, Inc., a corporation of Delaware U.S.), ion semiconductor sequencing, DNA nanoball sequencing, heliscope sequencing, single molecule real time sequencing (SMRT sequencing), solid state nanopore sequencing (Oxford sequencing), protein based nanopore sequencing, sequencing by electrical tunneling currents, sequencing by matrix-assisted laser desorption ionization time-of-flight mass spectrometry (MALDI-TOF MS), microfluidic Sanger sequencing, transmission electron microscopy DNA sequencing, RNA polymerase (RNAP) sequencing method, in vitro virus high throughput sequencing (IVV-HiTSeq), and sequencing by hybridization. Multiple, fragmented sequence reads must be assembled together on the basis of their overlapping areas.

The foregoing methods can be used singularly or in combination. The sequencing methods can be applied to genome sequencing, genome resequencing, transcriptome profiling (RNA-Seq), DNA-protein interactions (ChIP-sequencing), and epigenome characterization. Preferably, the sequencing method(s) operates in a parallel mode (characterizing many sequences concurrently).

Microorganisms

Microorganisms include bacteria, fungi, viruses, protozoans, and parasites.

Exemplary non-limiting bacterial species include *Acetobacter aurantius, Acinetobacter baumannii, Actinomyces israelii, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus Thuringiensis, Bacteroides fragilis, Bacteroides gingivalis, Bacteroides melaninogenicus* (also known as *Prevotella melaninogenica), Bartonella henselae, Bartonella quintana, Bordetella, Bordetella bronchiseptica, Bordetella pertussis, Borrelia afzelii, Borrelia burgdorferi, Borrelia garinii, Borrelia recurrentis, Brucella abortus, Brucella canis, Brucella melitensis, Brucella suis, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydophila pneumoniae* (previously called *Chlamydia pneumoniae), Chlamydophila psittaci* (previously called *Chlamydia psittaci), Chlamydia trachomatis, Clostridium botulinum, Clostridium difficile, Clostridium perfringens* (previously called *Clostridium welchii), Clostridium tetani, Corynebacterium diphtheriae, Corynebacterium fusiforme, Coxiella burnetii, Ehrlichia canis, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Leptospira interrogans, Leptospira santarosai, Leptospira weilii, Leptospira noguchii, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycobacterium ulcerans, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica* (previously called *Bacteroides melaninogenicus), Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Shigella sonnei, Spirillum volutans, Streptococcus agalactiae, Staphylococcus aureus, Staphylococcus epidermidis, Staphylococcus saprophyticus, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus viridans, Treponema pallidum, Treponema denticola, Ureaplasma urealyticum, Vibrio cholerae, Vibrio comma, Vibrio parahaemolyticus, Vibrio vulnificus, Yersinia enterocolitica, Yersinia pestis, Yersinia pseudotuberculosis,*

Non-limiting exemplary viruses include Adenovirus, Herpes simplex, type 1, Herpes simplex, type 2, Varicella-zoster virus, Epstein-barr virus, Human cytomegalovirus, Human herpesvirus, type 8, Human papillomavirus, BK virus, JC virus, Smallpox, Hepatitis B virus, Parvovirus B19, Human astrovirus, Norwalk virus, coxsackievirus, hepatitis A virus, poliovirus, rhinovirus, Hepatitis C virus, yellow fever virus, dengue virus, West Nile virus, TBE virus, Rubella virus, Hepatitis E virus, Human immunodeficiency virus (HIV), Influenza virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Rotavirus, Orbivirus, Coltivirus, Banna virus, and zika virus.

Non-limiting exemplary fungi include *Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartarurn.*

Non-limiting exemplary protozoa include *Entamoeba histolytica, Entamoeba coli, Entamoeba dispar, Entamoeba moshkovskii, Entamoeba bangladeshi, Entamoeba hartmanni, Dientamoeba fragilis, Endolimax nana, Lodarnoeba butschlii, Plasmodium malariae, Plasmodium falciparum, Plasmodium vivax, Plasmodium ovale, Naegleria fowleri, Acanthamoeba species, Balamuthia mandrillaris, Sappinia diploidea, Giardia larnblia, Giardia intestinalis, Giardia duodenalis, Toxoplasma gondii, Nippostrongylus brasiliensis, Cryptosporidium parvum, Cryptosporidium hominis, Cryptosporidium cams, Cryptosporidium felis, Cryptosporidium meleagridis, Cryptosporidium muris, Trichomonas vaginalis, Trypanosoma cruzi, Leishmania major, Leishmania tropica, Leishmania barziliensis, Leishmania mexicana, Leishmania guyanesis, Leishmania panamensis,* and *Trypanosoma brucei.*

Computer Hardware and Software

The computer system for implementing the present invention can take the form of an entirely hardware embodiment, an entirely software embodiment (including firmware, resident software, microcode, etc.), or a combination of software and hardware that may all generally be referred to herein as a "circuit," "module," or "system."

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
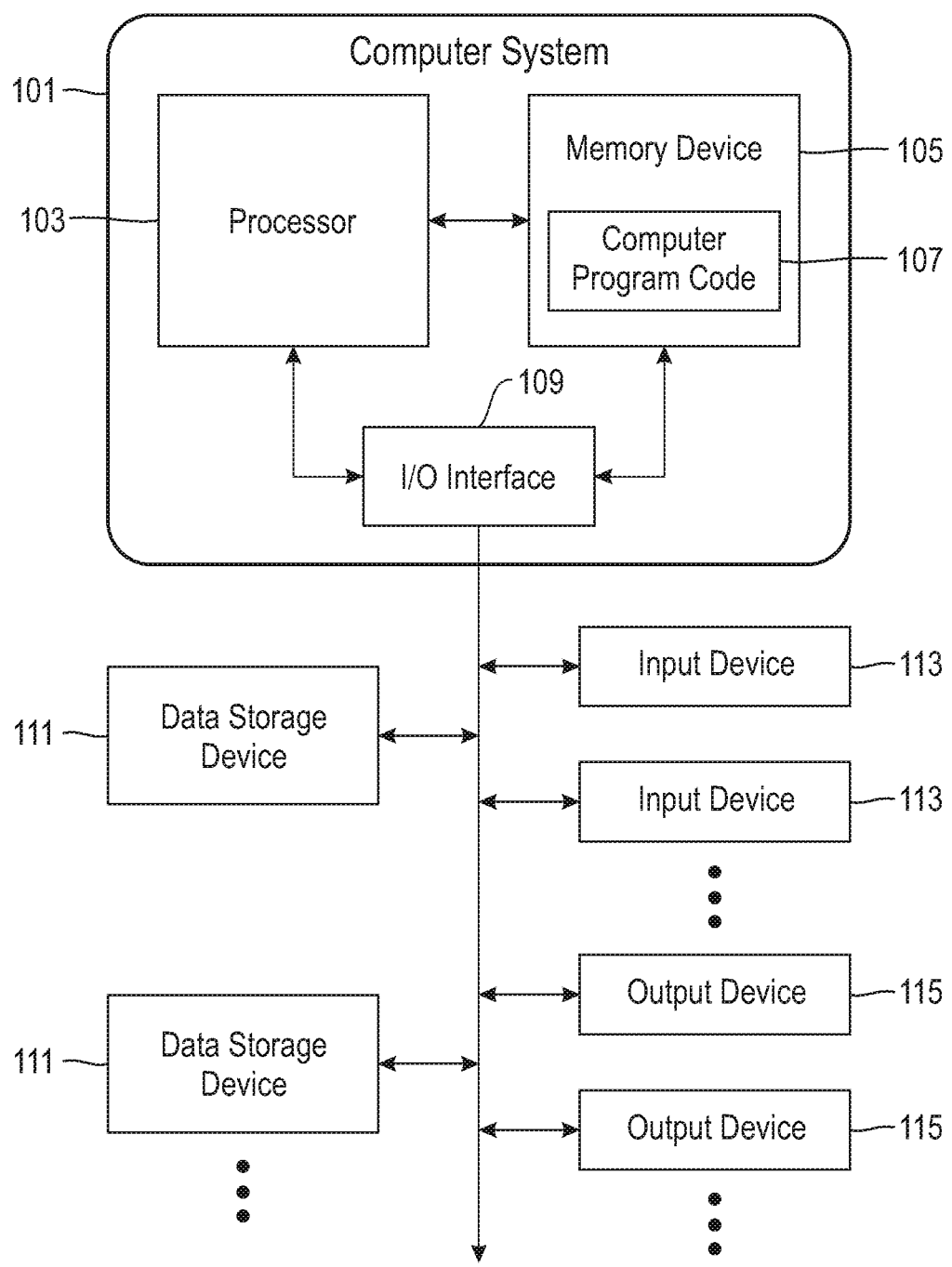
FIG. 3 is a drawing of the structure of a computer system and computer program code that may be used to implement the method.

FIG. 3 shows a structure of a computer system and computer program code that may be used to implement the disclosed method. In FIG. 3, computer system 101 comprises a processor 103 coupled through one or more I/O Interfaces 109 to one or more hardware data storage devices 111 and one or more I/O devices 113 and 115. Hardware data storage devices 111 can contain, for example, raw reads, clean reads, final assembled genomes, reference genome databases, optimized parameter sets, quality metrics, and genome assembly software.

Hardware data storage devices 111 may include, but are not limited to, magnetic tape drives, fixed or removable hard disks, optical discs, storage-equipped mobile devices, and solid-state random-access or read-only storage devices. I/O devices may comprise, but are not limited to: input devices 113, such as keyboards, scanners, handheld telecommunications devices, touch-sensitive displays, tablets, biometric readers, joysticks, trackballs, or computer mice; and output devices 115, which may comprise, but are not limited to printers, plotters, tablets, mobile telephones, displays, or sound-producing devices. Data storage devices 111, input devices 113, and output devices 115 may be located either locally or at remote sites from which they are connected to I/O Interface 109 through a network interface.

Processor 103 may also be connected to one or more memory devices 105, which may include, but are not limited to, Dynamic RANI (DRAM), Static RANI (SRAM), Programmable Read-Only Memory (PROM), Field-Programmable Gate Arrays (FPGA), Secure Digital memory cards, SIM cards, or other types of memory devices.

At least one memory device 105 contains stored computer program code 107, which is a computer program that comprises computer-executable instructions. The stored computer program code can include a program for natural-language processing that implements the disclosed methods. The data storage devices 111 may store the computer program code 107. Computer program code 107 stored in the storage devices 111 can be configured to be executed by processor 103 via the memory devices 105. Processor 103 can execute the stored computer program code 107.

Thus the present invention discloses a process for supporting computer infrastructure, integrating, hosting, maintaining, and deploying computer-readable code into the computer system 101, wherein the code in combination with the computer system 101 is capable of performing the disclosed method.

Any of the components of the present invention could be created, integrated, hosted, maintained, deployed, managed, serviced, supported, etc., by a service provider. Thus, the present invention discloses a process for deploying or integrating computing infrastructure, comprising integrating computer-readable code into the computer system 101, wherein the code in combination with the computer system 101 is capable of performing the disclosed method.

One or more data storage units 111 (or one or more additional memory devices not shown in FIG. 3) may be used as a computer-readable hardware storage device having a computer-readable program embodied therein and/or having other data stored therein, wherein the computer-readable program comprises stored computer program code 107. Generally, a computer program product (or, alternatively, an article of manufacture) of computer system 101 may comprise said computer-readable hardware storage device.

While it is understood that program code 107 may be deployed by manually loading the program code 107 directly into client, server, and proxy computers (not shown) by loading the program code 107 into a computer-readable storage medium (e.g., computer data storage device 111), program code 107 may also be automatically or semi-automatically deployed into computer system 101 by sending program code 107 to a central server (e.g., computer system 101) or to a group of central servers. Program code 107 may then be downloaded into client computers (not shown) that will execute program code 107.

Alternatively, program code 107 may be sent directly to the client computer via e-mail. Program code 107 may then either be detached to a directory on the client computer or loaded into a directory on the client computer by an e-mail option that selects a program that detaches program code 107 into the directory.

Another alternative is to send program code 107 directly to a directory on the client computer hard drive. If proxy servers are configured, the process selects the proxy server code, determines on which computers to place the proxy servers' code, transmits the proxy server code, and then installs the proxy server code on the proxy computer. Program code 107 is then transmitted to the proxy server and stored on the proxy server.

In one embodiment, program code 107 is integrated into a client, server and network environment by providing for program code 107 to coexist with software applications (not shown), operating systems (not shown) and network operating systems software (not shown) and then installing program code 107 on the clients and servers in the environment where program code 107 will function.

The first step of the aforementioned integration of code included in program code 107 is to identify any software including the network operating system (not shown), which is required by program code 107 or that works in conjunction with program code 107 and is on the clients and servers where program code 107 will be deployed. This identified software includes the network operating system, where the network operating system comprises software that enhances a basic operating system by adding networking features. Next, the software applications and version numbers are identified and compared to a list of software applications and correct version numbers that have been tested to work with program code 107. A software application that is missing or that does not match a correct version number is upgraded to the correct version.

A program instruction that passes parameters from program code 107 to a software application is checked to ensure that the instruction's parameter list matches a parameter list required by the program code 107. Conversely, a parameter passed by the software application to program code 107 is checked to ensure that the parameter matches a parameter required by program code 107. The client and server operating systems, including the network operating systems, are identified and compared to a list of operating systems, version numbers, and network software programs that have been tested to work with program code 107. An operating system, version number, or network software program that does not match an entry of the list of tested operating systems and version numbers is upgraded to the listed level on the client computers and upgraded to the listed level on the server computers.

After ensuring that the software, where program code 107 is to be deployed, is at a correct version level that has been tested to work with program code 107, the integration is completed by installing program code 107 on the clients and servers.

Embodiments of the present invention may be implemented as a method performed by a processor of a computer system, as a computer program product, as a computer system, or as a processor-performed process or service for supporting computer infrastructure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method, comprising:
    selecting a k-mer-based de novo genome assembler program, designated assembler;
    providing a set of parameters for assembly of a set of sequenced nucleic acids, the parameters having respective values and respective priority scores, the parameters including a k-mer parameter having an initial length k in number of nucleotides, k being a positive integer equal to at least 35;
    providing a set of quality metrics for assembly of a set of sequenced nucleic acids, the quality metrics having respective weights indicating importance, respective target values, and respective computed values calculated during assembly, a given quality metric depending on one or more of the parameters;
    initiating assembly of the set of sequenced nucleic acids by the assembler, the assembler utilizing the set of parameters and the set of quality metrics, thereby forming intermediate assembled sequences;
    performing a procedure iteratively until the respective computed values of the quality metrics equal the respective target values, the procedure comprising the steps of: i) stopping the assembler when the respective computed values of the quality metrics do not equal the respective target values, ii) modifying at least one of the parameters and/or at least one of the quality metrics, iii) deleting any intermediate assembled sequences, iv) initiating assembly of the set of sequenced nucleic acids by the assembler, and v) calculating values of the quality metrics including any modified quality metrics, the procedure terminating while utilizing a set of final parameters and a set of final quality metrics, the final parameters including a final k-mer parameter of length k'; and
    completing assembly of the set of sequenced nucleic acids using the assembler, the set of final parameters, and the set of final quality metrics, thereby forming one or more final assembled genomes;
    wherein the intermediate assembled sequences have sizes, a mean size, a median size, and a standard deviation of the sizes of the intermediate assembled sequences calculated during the assembly;
    wherein a given taxonomic rank contains reference genomes having sizes, a mean size, a median size, and a standard deviation of the sizes of the reference genomes; and
    wherein the assembly includes a quality metric for the difference between the mean size of the intermediate assembled sequences and the mean size of the reference genomes.

2. The method of claim 1, wherein the method comprises storing the final parameters and the final quality metrics with the one or more final assembled genomes.

3. The method of claim 1, wherein the method is performed by a computer system without human intervention.

4. The method of claim 1, wherein the intermediate assembled sequences are partially assembled genomes.

5. The method of claim 1, wherein the intermediate assembled sequences are wholly assembled genomes.

6. The method of claim 1, wherein the quality metrics include a member selected from the group consisting of N50, NA50, NG50, NGA50, L50, LA50, LG50, LGA50, and combinations thereof.

7. The method of claim 1, wherein the quality metrics include a member selected from the group consisting of number of contigs, number of contigs above a given size, number of contig edges, number of connections within contigs, and combinations thereof.

8. The method of claim 1, wherein the assembly includes a quality metric for the difference between the median size of the intermediate assembled sequences and the median size of the reference genomes.

9. The method of claim 5, wherein the assembly includes a quality metric for the difference between the standard deviation of the sizes of the intermediate assembled sequences and the standard deviation of the sizes of the reference genomes.

10. The method of claim 1, wherein the quality metrics include a member selected from the group consisting of coverages per nucleotide base, coverages per contig, coverages per assembly, number of misassembles, relative abundances of nucleotides, repetitive content of nucleotides, and combinations thereof.

11. The method of claim 1, wherein k' is optimal for one of the final assembled genomes.

12. The method of claim 1, wherein k' is an average of values of the k-mer parameter used in the procedure.

13. The method of claim 1, wherein the k-mer parameter has a lower priority score and/or lower ranking compared to another parameter.

14. The method of claim 13, wherein said another parameter is a member selected from the group consisting of coverage cutoff value, number of mismatches allowed, expected genome size, insert size, and sequencing error rate of the intermediate assembled sequences.

15. The method of claim 1, wherein k' is optimal for a subset of the final assembled genomes, the subset comprising more than one final assembled genome.

16. The method of claim 15, wherein the subset is defined by taxonomic rank.

17. The method of claim 15, wherein the subset is defined by sequencing method.

18. The method of claim 17, wherein the sequencing method is a member selected from the group consisting of Sanger, Illumina, PacBio, 454, Ion Torrent, and SOLid.

19. A system comprising one or more computer processor circuits configured and arranged to:
select a k-mer-based de novo genome assembler program, designated assembler;
provide a set of parameters for assembly of a set of sequenced nucleic acids, the parameters having respective values and respective priority scores, the parameters including a k-mer parameter having an initial length k in number of nucleotides, k being a positive integer equal to at least 35;
provide a set of quality metrics for assembly of a set of sequenced nucleic acids, the quality metrics having respective weights indicating importance, respective target values, and respective computed values calculated during assembly, a given quality metric depending on one or more of the parameters;
initiate assembly of the set of sequenced nucleic acids by the assembler, the assembler utilizing the set of parameters and the set of quality metrics, thereby forming intermediate assembled sequences, wherein the intermediate assembled sequences are wholly assembled genomes;
perform a procedure iteratively until the respective computed values of the quality metrics equal the respective target values, the procedure comprising the steps of: i) stopping the assembler when the respective computed values of the quality metrics do not equal the respective target values, ii) modifying at least one of the parameters and/or at least one of the quality metrics, iii) deleting any intermediate assembled sequences, iv) initiating assembly of the set of sequenced nucleic acids by the assembler, and v) calculating values of the quality metrics including any modified quality metrics, the procedure terminating while utilizing a set of final parameters and a set of final quality metrics, the final parameters including a final k-mer parameter of length k'; and
complete assembly of the set of sequenced nucleic acids using the assembler, the set of final parameters, and the set of final quality metrics, thereby forming one or more final assembled genomes;
wherein the assembly includes a quality metric for the difference between the standard deviation of the sizes of the intermediate assembled sequences and the standard deviation of the sizes of the reference genomes.

20. A computer program product, comprising a computer readable hardware storage device having a computer-readable program code stored therein, said program code configured to be executed by a processor of a computer system to implement a method comprising:
selecting a k-mer-based de novo genome assembler program, designated assembler;
providing a set of parameters for assembly of a set of sequenced nucleic acids, the parameters having respective values and respective priority scores, the parameters including a k-mer parameter having an initial length k in number of nucleotides, k being a positive integer equal to at least 35;
providing a set of quality metrics for assembly of a set of sequenced nucleic acids, the quality metrics having respective weights indicating importance, respective target values, and respective computed values calculated during assembly, a given quality metric depending on one or more of the parameters;
initiating assembly of the set of sequenced nucleic acids by the assembler, the assembler utilizing the set of parameters and the set of quality metrics, thereby forming intermediate assembled sequences;
performing a procedure iteratively until the respective computed values of the quality metrics equal the respective target values, the procedure comprising the steps of: i) stopping the assembler when the respective computed values of the quality metrics do not equal the respective target values, ii) modifying at least one of the parameters and/or at least one of the quality metrics, iii) deleting any intermediate assembled sequences, iv) initiating assembly of the set of sequenced nucleic acids by the assembler, and v) calculating values of the quality metrics including any modified quality metrics, the procedure terminating while utilizing a set of final parameters and a set of final quality metrics, the final parameters including a final k-mer parameter of length k'; and
completing assembly of the set of sequenced nucleic acids using the assembler, the set of final parameters, and the set of final quality metrics, thereby forming one or more final assembled genomes;
wherein the intermediate assembled sequences have sizes, a mean size, a median size, and a standard deviation of the sizes of the intermediate assembled sequences calculated during the assembly;
wherein a given taxonomic rank contains reference genomes having sizes, a mean size, a median size, and a standard deviation of the sizes of the reference genomes; and
wherein the assembly includes a quality metric for the difference between the mean size of the intermediate assembled sequences and the mean size of the reference genomes.

21. A method of genome assembly for single assembly or sets of assemblies by optimizing the k-mer length parameter, the method comprising the following steps:
using high throughput sequencing to sequence one or more genomes, thereby forming sequence data;
processing the sequence data for quality control;

selecting a quality metric for assembly of the sequence data, the quality metric having a calculated value during an assembly and a target value;

initiating assembly of the sequence data using a set of k-mer values for the one or more genomes, the k-mer values having scores and ranks;

performing a procedure during the assembly when the calculated value of the quality metric does not equal to the target value, the procedure comprising:
 a) deleting any intermediate assembled sequences,
 b) modifying the k-mer values,
 c) initiating assembly using the modified k-mer values,
 d) assessing the calculated value of the quality metric relative to the target value before the assembly is complete;
 e) updating the scores and ranks of the k-mer values;

repeating the procedure until the calculated value of the quality metric equals the target value; and completing the assembly;

wherein the intermediate assembled sequences are wholly assembled genomes; and wherein the assembly includes a quality metric for the difference between the standard deviation of the sizes of the intermediate assembled sequences and the standard deviation of the sizes of the reference genomes.

* * * * *